(12) United States Patent
Claret et al.

(10) Patent No.: US 9,801,899 B2
(45) Date of Patent: Oct. 31, 2017

(54) ARTIFICIAL TEAR EMULSION

(75) Inventors: Claude Claret, Nice (FR); Martine Claret, Nice (FR); Carole Gard, Antibes (FR); Nicola Lamprecht-Weissenborn, Besancon (FR)

(73) Assignee: Horus Pharma (FR)

( * ) Notice: Subject to any disclaimer, the term of this patent is extended or adjusted under 35 U.S.C. 154(b) by 0 days.

(21) Appl. No.: 13/642,580

(22) PCT Filed: Apr. 21, 2011

(86) PCT No.: PCT/EP2011/056447
§ 371 (c)(1),
(2), (4) Date: Dec. 18, 2012

(87) PCT Pub. No.: WO2011/131765
PCT Pub. Date: Oct. 27, 2011

(65) Prior Publication Data
US 2013/0156867 A1    Jun. 20, 2013

(30) Foreign Application Priority Data

Apr. 21, 2010  (FR) ..................... 10 53030

(51) Int. Cl.
| | | |
|---|---|---|
| *A61K 45/06* | (2006.01) | |
| *A61K 47/26* | (2006.01) | |
| *A61K 47/38* | (2006.01) | |
| *A61K 31/728* | (2006.01) | |
| *A61K 47/24* | (2006.01) | |
| *A61K 31/726* | (2006.01) | |
| *A61K 9/00* | (2006.01) | |
| *A61K 9/107* | (2006.01) | |
| *A61K 47/34* | (2017.01) | |

(52) U.S. Cl.
CPC .......... *A61K 31/726* (2013.01); *A61K 9/0048* (2013.01); *A61K 9/107* (2013.01); *A61K 31/728* (2013.01); *A61K 45/06* (2013.01); *A61K 47/24* (2013.01); *A61K 47/26* (2013.01); *A61K 47/34* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,232,687 A | 8/1993 | Geimer | |
| 2005/0043271 A1* | 2/2005 | Gross et al. | .......... 514/54 |
| 2005/0164979 A1* | 7/2005 | Gross et al. | .......... 514/54 |
| 2006/0069162 A1* | 3/2006 | Asada et al. | .......... 514/573 |
| 2007/0210121 A1 | 9/2007 | Stadelhofer et al. | |
| 2009/0294347 A1 | 12/2009 | Wochele et al. | |
| 2010/0216741 A1* | 8/2010 | Matsumura | .......... A61K 9/0048 514/54 |
| 2010/0303915 A1* | 12/2010 | Yu | .......... 424/489 |

FOREIGN PATENT DOCUMENTS

| | | | | |
|---|---|---|---|---|
| DE | 195 27 132 | * | 1/1997 | .......... A61K 9/107 |
| EP | 0391369 | * | 10/1990 | |
| EP | 2085068 | | 8/2009 | |
| FR | 2816600 | | 11/2000 | |
| FR | 2873358 | | 7/2004 | |
| JP | 2007211007 | * | 8/2007 | |
| JP | 2007211007 A | | 8/2007 | |
| WO | WO 95/05163 | * | 2/1995 | .......... A61K 9/00 |
| WO | 2008/015505 | | 2/2008 | |

* cited by examiner

*Primary Examiner* — Robert A Wax
*Assistant Examiner* — Danah Al-Awadi
(74) *Attorney, Agent, or Firm* — Banner & Witcoff, Ltd.

(57) ABSTRACT

The present invention relates to an oil-in-water emulsion comprising at least one mucomimetic polymer, at least one lipid of phospholipid type, at least one lipid other than the phospholipid, at least one stabilizing polymer, and a hydrophilic liquid, to an emulsion comprising an aqueous phase that contains at least one stabilizing polymer and at least one mucomimetic polymer, and an oily phase that contains at least one lipid of phospholipid type and a lipid other than the phospholipid, to a medicament comprising one of these emulsions, and to the use of one of these emulsions as an agent for restoring and/or replacing the lachrimal film or as a carrier for an active compound.

25 Claims, No Drawings

ARTIFICIAL TEAR EMULSION

RELATED APPLICATION DATA

This application is a National Stage Application under 35 U.S.C. 371 of PCT application PCT/EP2011/056447 designating the United States and filed Apr. 21, 2011; which claims the benefit of FR patent application number 1053030 and filed Apr. 21, 2010 each of which are hereby incorporated by reference in their entireties.

The present invention relates to lipid emulsions, in particular to artificial tear emulsions, comprising a mucomimetic polymer, to the use thereof and to a method for providing thereof. The present invention relates more specifically to the use of these compositions in the field of ophthalmology. These compositions can more particularly be used to prevent or treat eye dryness and/or disorders related to eye dryness. These compositions can also be used in the transport of active substances, in particular in the eye.

The surface of the eye is a transitional mucous membrane between the external environment and the structures within the eye. The eyelids are the first line of defense for the ocular surface and help maintain the lacrimal film that covers the conjunctival epithelium, notably via the lacrimal and meibomian glands located in the lower and upper eyelids, respectively.

This lacrimal film is an uninterrupted fluid film with a thickness between 3 and 10 μm and a volume of roughly 10 μl. This film is continuously replenished, at a rate of approximately 1 μl/min.

The functions of the lacrimal film include keeping the ocular surface moist, producing a smooth surface to allow vision without distortion, protecting the cornea and the conjunctive epithelium from external attack (irritants, dust, bacteria, etc.), and transporting biological substances used in the physiological processes of the eye, including oxygen for the cornea.

Furthermore, the lacrimal film is composed of three layers, namely a lipid layer, an aqueous layer and a mucin layer:
  the lipid layer, roughly 100 nm thick, secreted by the meibomian glands, that notably reduces evaporation and stabilizes the lacrimal film;
  the aqueous layer, which nourishes, hydrates and protects the corneal and conjunctival epithelium; in addition to its high water content, it is rich in nutritive elements, enzymes, antibacterial agents and scarring factors and contains a strong mucin concentration gradient; and
  the mucin layer, which anchors the lacrimal film.

The three-layer structure of the lacrimal film can also be seen as a system comprising two main phases:
  a non-polar hydrophobic phase in contact with the air and made up of phospholipids, esters, triglycerides and free fatty acids, and
  a polar and anionic hydrophilic phase made up of glycoproteins, lipids, electrolytes, enzymes, polysaccharides and water.

The deterioration of one of these layers can cause dry eye syndrome, for example due to hyposecretion by the lacrimal glands or a dysfunction of the meibomian glands, and thus of the lipid layer of the lacrimal film, and lead to hyper-evaporation.

The symptoms of dry eye include pain, itching, the sensation of a foreign object in the eye, burning, photophobia and general discomfort. Thus, this disease is disabling and negatively impacts the patient's quality of life.

Furthermore, dry eye, whatever its etiology, can cause keratitis and/or conjunctivitis.

Dry eye syndrome is quite common, as it is estimated that roughly 15-20% of those over 65 suffer from it. The moderate and severe forms, involving keratitis or keratoconjunctivitis sicca, represent 25-30% of cases.

The first line of treatment for dry eye syndromes, independent of severity, are lacrimal substitutes, also called artificial tears, which act first on the symptoms.

Historically, the simple lacrimal substitutes containing sodium chloride have been gradually replaced by solutions containing cellulose derivatives or carbomers, making it possible to increase the viscosity of the solutions and to obtain a more persistent action.

However, even more recently two main categories appear to be more effective:
  lipid emulsions, and
  solutions containing sodium hyaluronate.

Unfortunately, the great majority of these solutions concern only the partial restoration of one of the lacrimal film's components.

In particular, hydrophobic lipid emulsions act on the lacrimal film's hydrophobic or lipid phase by limiting hyper-evaporation, whereas mucomimetic hyaluronic acid-based solutions act on the lacrimal film's hydrophilic phase and promote lacrimal film anchoring.

In addition, since these products must be sterile, most existing solutions contain preservatives for destroying microorganisms once the product is opened and during the product's use.

These preservatives can be in particular:
  toxic to or irritating for cells of the cornea or the conjunctiva, mucous cells (which release mucins essential to lacrimal film stability) or covering epithelial cells, and/or
  a source of allergy and inflammation, in particular for chronic pathologies such as glaucoma, allergy and dry eye, which require frequent application of products containing preservatives.

The clinical consequences can thus be an aggravation of symptoms and/or evolution toward a chronic illness.

Quite frequently the solutions contain what are called surface-active agents in order to give the composition satisfactory physicochemical stability. These surface-active agents can have deleterious effects similar to those of preservatives, namely an irritating, allergenic, even cytotoxic nature. In particular, these agents, also called emulsifiers, surfactants or wetting agents, present in small quantities, are used to stabilize the oil droplets in oil-based solutions or lipid emulsions, sold with the indication of ocular dryness by hyper-evaporation.

Thus, the existing compositions can be insufficiently effective and may indeed have adverse effects such as the destruction of healthy cells, a reactivation of the causes of dry eye by destabilization of the lacrimal film's lipid layer or allergic reactions. They can be unstable, requiring specific storage conditions (refrigeration, for example) and/or requiring very frequent use due to an unsatisfactorily short period of action.

The present invention thus aims to solve all or part of the problems cited above. In particular, the invention aims to provide a composition, notably an emulsion, having improved effectiveness, no adverse effects, or at least said effects are limited as much as possible, improved stability, that is easy to produce, comprising and/or using during its production a minimum of deleterious, allergenic and/or toxic products, and/or having a reconstructive action on the whole of the lacrimal film.

According to a first aspect, the present invention relates to an oil-in-water emulsion, notably for ophthalmic use, comprising, or consisting of:
- at least one mucomimetic polymer,
- at least one phospholipid,
- at least one lipid other than the phospholipid,
- at least one stabilizing polymer,
- water,
- optionally sodium chloride, and
- optionally:
  - an active substance and/or
  - a substance that helps restore the composition of the lacrimal film's aqueous layer or lacrimal substitutes.

In the present description, "at least one" refers to one or more, and in particular to one.

The emulsion of the invention is an oil-in-water emulsion whose aqueous phase comprises at least one stabilizing polymer and at least one mucomimetic polymer, and the oily phase comprises at least one phospholipid and at least one lipid other than the phospholipid.

The mucomimetic polymer can be a polymer of polysaccharides, also called glycans, and more particularly among glycosaminoglycans (GAGs) and hyaluronic acids. These polymers, also called acid mucopolysaccharides, are characterized by a strong capacity to retain water, which gives them mucomimetic properties.

In particular, polysaccharides comprise at least 5, notably at least 10, in particular at least 20 monosaccharide units.

Among polysaccharides, mention may be made of:
- dextran sulfate, which is a complex polysaccharide, in particular of molecular weight from 4 to 500 kDa,
- arabinogalactan, a biopolymer comprised of arabinose and galactose monosaccharides and a natural component of certain gums and the walls of certain mycobacterial cells,
- heparin, in particular of molecular weight from 6 to 30 kDa,
- keratan sulfate,
- chondroitin sulfate, in particular of molecular weight of roughly 50 kDa,
- dermatan sulfate, and
- hyaluronic acid, a high-viscosity disaccharide polymer naturally present in many tissues, including conjunctive tissues, and one of the main components of the extracellular matrix.

The latter can be obtained by extraction from animal tissues or by bacterial fermentation.

The mucomimetic polymer is more preferentially selected from glycosaminoglycans and hyaluronic acids and mixtures thereof. More preferentially, the mucomimetic polymer is selected from hyaluronic acids.

The mucomimetic polymer can have a molecular weight of 10 to 10,000 kDa, notably of 500 to 1,500 kDa, indeed of roughly 1,000 kDa.

In particular, the emulsion comprises a mucomimetic polymer in a concentration of 0.01% to 5% by weight in relation to the total weight of the emulsion, in particular of 0.05% to 2.5% by weight, in particular of 0.1% to 1% by weight, indeed of 0.15% to 0.5% by weight, and even more particularly of roughly 0.2% by weight.

Phospholipids are lipids comprising a phosphate group, i.e., a unit of two fatty acids, glycerol and phosphate.

They can comprise sphingosine (serine+fatty acid), a fatty acid, a phosphate and a nitrogenous alcohol or two fatty acids, a glycerol molecule, a phosphate and a nitrogenous alcohol.

In particular, the phospholipid is selected from phosphoacylglycerides, also called phosphacylglycerols, phosphosphingolipids, phosphonosphingolipids, phosphoglycolipids and phosphosaccharolipids.

Particularly, the phospholipid is selected from lecithins, also called phosphatidylcholines, extracted from soya, egg or sunflower. The lecithins are preferably extracted from soya.

The lecithin can be used alone or in combination. In particular, several different lecithins are present in the emulsion.

The emulsion can comprise the phospholipid in a concentration of 0.01% to 3% by weight in relation to the total weight of the emulsion, notably of 0.02% to 1% by weight, in particular of 0.05% to 0.5% by weight, indeed of 0.075% to 0.2% by weight, and even more particularly of roughly 0.1% by weight.

The emulsion comprises at least one lipid other than the phospholipid, in particular a glyceride.

The glyceride can be a lipid of the acylglycerol or glyceride class, in particular selected from castor, soya, sesame, paraffin, lanolin, petroleum jelly, corn, glycerin or monoglyceride, or triglyceride oils.

Particularly, said glyceride is a triglyceride, preferentially a medium-chain triglyceride, whose three hydroxyl groups of the glycerol are esterified by fatty acids, comprising from four to 22 carbon atoms, in particular comprising eight to 12 carbon atoms, preferably selected from capric acid, caprylic acid and mixtures thereof.

The emulsion can comprise a lipid other than the phospholipid in a concentration of 0.01% to 5% by weight in relation to the total weight of the emulsion, notably of 0.05% to 2.5%, in particular of 0.1% to 1% by weight, indeed of 0.15% to 0.5% by weight, and even more particularly of roughly 0.2% by weight.

Particularly, the emulsion comprises a weight ratio of the lipid other than the phospholipid to the phospholipid of 0.1 to 10, notably of 0.2 to 5, in particular of 0.5 to 2, indeed of roughly 1.

The emulsion comprises at least one stabilizing polymer, in particular an ionic polymer, more particularly an anionic polymer.

The stabilizing polymer can be selected from polyvinyl alcohol polymers, polysorbates and cellulose polymers, notably methylcellulose, ethylcellulose, hydroxypropylcellulose and carboxymethylcellulose. In particular, the polymer is carboxymethylcellulose.

The stabilizing polymer is in particular of sodium polymer, notably sodium carboxymethylcellulose.

Sodium carboxymethylcellulose has a general formula of $[C_6H_7O_2(OH)_x(OCH_2COONa)_y]_n$ with y, degree of substitution, enabling solubilization in water, between 0.6 and 1, x between 1 and 2.4 (while x+y=3) and n between 80 and 1,500.

The soluble forms can have a viscosity of 5 to 2,000 cP in 1% (weight) solution, notably of 1,000 to 2,000 cP, indeed of roughly 1,500 cP. Carboxymethylcellulose can have a concentration of salt in relation to the dry substance of at least 6.5% and more than 10.8% so as to correspond to one of the specifications of the European pharmacopeia.

The stabilizing polymer, which is in particular ionic, can have a molecular weight of 17,000 to 300,000 g/mol.

The composition can comprise a stabilizing polymer, in particular ionic, in a concentration of 0.01% to 5% by weight, notably of 0.05% to 2.5%, in particular of 0.1% to 1% by weight, indeed of 0.15% to 0.5% by weight, and even more particularly of roughly 0.2% by weight in relation to the total weight of the composition.

The presence of the stabilizing polymer, notably ionic, and in particular of the carboxymethylcellulose, notably sodium, provides the emulsion comprising at least one phospholipid and a mucomimetic polymer with satisfactory stability. This stability can be observed notably by the size of the globules of the oily phase which remains essentially stable, notably an increase in size of less than 10% after three weeks.

The emulsion may exhibit coalescence, but simple agitation can redisperse the globules.

The emulsion of the invention can have a pH of 6 to 8, notably of 6.7 to 7.7, in particular of 7.0 to 7.6, indeed of roughly 7.4.

The emulsion can particularly have a pH of 5.5 to 8, notably of 6 to 7.7, in particular of 6.2 to 7.5, indeed of roughly 7.0.

Particularly, the emulsion of the invention comprises a buffer. Said buffer can be a phosphate, acetate or citrate buffer, and in particular it is a citrate buffer.

Particularly, the citrate buffer can improve the emulsion's stability.

The emulsion of the invention thus advantageously comprises citrate in a suitable quantity to adjust the pH to the desired value.

The emulsion is an oil-in-water emulsion, the oil part appearing as globules comprising the lipid components defined above and the other possible hydrophobic and/or lipophilic components of the emulsion.

The small size of these globules contributes to the satisfactory stability of the emulsion.

For the preparation of a preservative-free emulsion, such as defined below, preferably 98% to 99% of the emulsion must be able to pass through a 0.22 μm filter, the filter size generally used for sterilizing emulsions. Globules of a size greater than 220 nm can pass through a 0.22 μm filter by temporarily modifying their shape, however slowing the filtration process.

The globules preferably have a maximum size less than or equal to 220 nm, in particular less than or equal to 160 nm.

The emulsion of the invention is particularly suited for topical use in treating or preventing ophthalmic diseases, notably as an eye lotion, enabling greater tolerance due to the fact that the emulsion is stable without the help of a surfactant, or with a surfactant in a sufficiently small concentration to be tolerated by the ocular surface.

According to a preferred embodiment, the present emulsion is free of preservatives, notably chemical, used alone or in combination. Said preservatives can in particular be selected from the list of products authorized by regulations, such as:
quaternary ammoniums, notably benzalkonium chloride, alkyldimethylbenzylammonium, cetrimide, cetylpyridinium chloride, benzododecinium bromide, benzethonium chloride, cetalkonium chloride,
mercurial preservatives, such as phenylmercuric nitrate/acetate/borate, thiomersal,
alcohol preservatives, such as chlorobutanol, benzyl alcohol, phenylethanol, phenylethyl alcohol,
carboxylic acids, such as sorbic acid,
phenols, in particular methyl/propylparaben,
amidines, for example chlorhexidine digluconate, and/or
EDTA, a chelating agent that potentiates preservative effectiveness, in combination with at least one preservative.

In particular, the emulsion is preferentially free of EDTA as such.

In the context of the present invention, the expressions "preservative free" and "without preservatives" refer to a concentration in preservatives and/or EDTA of less than or equal to 10 ppm, notably less than or equal to 1 ppm, indeed equal to 0 ppm.

According to another embodiment, the composition can comprise at least one preservative, but preferably at a low concentration, for example at a concentration less than or equal to 0.1% by weight, notably less than or equal to 0.05% by weight, even less than 0.01% by weight in relation to the total weight of the emulsion.

The preservative is in particular present in the aqueous phase.

According to an advantageous embodiment of the invention, the emulsion is free of surfactants, used alone or in combination. Said surfactants are the typical surfactants used to prepare emulsions, in particular in the fields of cosmetics and pharmaceuticals, in particular selected from the list of products authorized by regulations, such as:
polysorbates,
polyethylene glycols and derivatives thereof,
polyoxyethylene-40-stearate,
sorbitan esters,
polyoxyethylene-polyoxypropylene copolymers,
polyvinyl alcohols, and
polyvinylpyrrolidone polymers.

In the context of the present invention, the expressions "surfactant free" and "without surfactants" refer to a surfactant concentration of less than or equal to 0.1% by weight in relation to the total weight of the emulsion, notably less than 0.01% by weight, indeed equal to 0% by weight.

The phospholipids entering into the composition of the inventive emulsion, such as defined above, and in particular lecithins, are not typical surfactants used as surfactants in the preparation of emulsions in the fields of cosmetics or pharmaceuticals. In any event, they are of course not excluded from the composition of the inventive emulsion.

According to another embodiment of the invention, the emulsion can comprise at least one surfactant, preferably at a low concentration, i.e., at a concentration less than or equal to 0.5% by weight in relation to the total weight of the emulsion, notably less than or equal to 0.25% by weight, indeed less than 0.15% by weight.

According to a particularly preferred embodiment of the invention, the emulsion is surfactant-free and preservative-free.

This can particularly make it possible to limit, decrease or indeed avoid adverse side effects, notably irritation to the eye and/or the mucous membranes, in particular near the eye.

Advantageously, the inventive emulsion has a low viscosity close to that of water, notably a dynamic viscosity of less than or equal to $10^{-1}$ Pa·s, in particular of $1.5 \times 10^{-3}$ to $8 \times 10^{-2}$ Pa·s, and particularly of $3 \times 10^{-3}$ to $6 \times 10^{-2}$ Pa·s.

The inventive emulsion advantageously has a turbidity such as defined by European Pharmacopeia 7.0 of 0 to 5,000 NTU, in particular of 0 to 1,000 NTU, particularly of roughly 200 to 700 NTU, indeed of roughly 500 NTU.

The inventive emulsion is particularly suited for use in the form of an eye lotion, preferably of low viscosity such as defined above and advantageously limpid.

The inventive emulsion particularly suited for topical use in treating or preventing ophthalmic diseases, in particular as an eye lotion, can have the properties of artificial tears, i.e., can have, once applied, a structure similar or identical to that of the lacrimal liquid.

According to a particular embodiment of the invention, the emulsion can be normo-osmolar, i.e., can have an osmolarity of 310 to 350 mOsm/l, which is an osmolarity corresponding to that of the normal lacrimal film.

According to another embodiment the composition can be hypo-osmolar and have an osmolarity of 100 to 300 mOsm/l, notably of 150 to 200 mOsm/l, indeed of roughly 180 mOsm/l.

According to a third embodiment, the emulsion can be hypo-osmolar and have an osmolarity of 100 to 300 mOsm/l, notably of 100 to 200 mOsm/l, indeed of 110 to 180 mOsm/l, particularly of 120 to 150 mOsm/l, indeed of roughly 135 mOsm/l.

A hypo-osmolar osmolarity can compensate for the hyper-osmolarity generally observed in patients suffering from dry eye.

The person skilled in the art can adjust the osmolarity of the inventive emulsion by adding a suitable quantity of salt, in particular potassium chloride, sodium chloride or potassium and/or sodium bicarbonate, preferentially sodium chloride.

The water content depends on the content of the other components of the inventive emulsion. Preferentially, in particular for an emulsion suited to topical use in treating or preventing ophthalmic diseases, in particular in the form of an eye lotion, the emulsion comprises a water content greater than or equal to 90% by weight in relation to the total weight of the emulsion, notably greater than 95% by weight, in particular greater than 98% by weight, and particularly greater than 99% by weight.

With this formulation, it is possible to add substances, in particular in the aqueous phase, that help restore the composition of the aqueous layer of the lacrimal film or lacrimal substitutes, such as:
vitamin A,
vitamin E,
vitamin B12,
albumin,
sodium, potassium, calcium, chloride and bicarbonate ions, and
buffer solution.

The composition or the emulsion can comprise one or more active agents, notably a therapeutically active agent. This active agent is in particular intended to act on the eye or is for ophthalmic use.

This composition or ophthalmic emulsion can be used to prepare a product for treating ophthalmic diseases in combination with the restoration of the lacrimal film in dry eye syndromes, in particular by incorporating therein an active ingredient possessing a therapeutic effect.

The active agent, notably for ophthalmic use, can be selected from antiseptics, antibiotics, antivirals, anti-inflammatories, anti-allergy agents, anti-glaucoma agents, anti-dryness agents, vasoconstrictors, anesthetics, mydriatics, miotics, diagnostic products and products for treating retinal diseases.

Among active ingredients for ophthalmic use, mention may be made of:
anesthetics, such as procaine, chloroprocaine, lidocaine, mepivacaine, tetracaine, proparacaine,
steroidal anti-inflammatories, such as betamethasone, dexamethasone, fluorometholone, loteprednol etabonate, medrysone, prednisolone, rimexolone, methylprednisolone, prednisone, fluocinolone, triamcinolone acetonide,
non-steroidal anti-inflammatories, such as flurbiprofen, suprofen, diclofenac, ketorolac, aspirin, indomethacin, ibuprofen, naproxen,
immunomodulators, such as cyclosporine, azathioprine, bromocriptine, methotrexate, dapsone, cyclophosphamide, chlorambucil, colchicine,
anti-glaucoma agents, such as dipivefrin, epinephryl, apraclonidine, brimonidine, betaxolol, carteolol, levobunolol, metipranolol, timolol, carbachol, pilocarpine, physostigmine, echothiophate, acetazolamide, brinzolamide, dorzolamide, methazolamide, latanoprost, bimatoprost, travoprost, unoprostone,
antibiotics and anti-infectives, such as cefotaxime, ceftazidime, cefuroxime, cefazoline, cephalothin, ampicillin, oxacillin, ticarcillin, sodium sulfacetamide, sulfisoxazole, sulfamethoxazole, neomycin, gentamicin, tobramycin, amikacin, norfloxacin, ciprofloxacin, ofloxacin, gatifloxacin, levofloxacin, moxifloxacin, bacitracin, gramicidin, polymyxin B, erythromycin, chloramphenicol, trimethoprim, oxytetracycline, vancomycin, and
antivirals, such as cidofovir, formivirsen, foscarnet, ganciclovir, valganciclovir, trifluridine, acyclovir, antifungals, natamycin, itraconazole, ketoconazole, miconazole, amphotericin B, fluconazole, flucytosine.

However, other active ingredients and other therapeutic classes can be envisaged.

According to a particular embodiment, the composition comprises essentially:
the mucomimetic polymer, in particular hyaluronic acid, notably at a concentration of roughly 0.2% by weight in relation to the total weight of the composition,
phosphatidylcholine, in particular at a concentration of roughly 0.1% by weight in relation to the total weight of the composition,
at least one triglyceride, in particular capric and/or caprylic acid, notably at a concentration of roughly 0.1% by weight in relation to the total weight of the composition,
the stabilizing polymer, in particular carboxymethylcellulose, notably at a concentration of roughly 0.1% by weight in relation to the total weight of the composition,
citrate and/or citric acid, notably in order to adjust the pH to roughly 7,
sodium chloride, notably in order to adjust the osmolarity, in particular to 180 mOsm/l, and
water.

Particularly, the present emulsion is sterilized without the use of chemical agents, notably used as preservatives. This emulsion can in particular be sterilized by filtration, in particular via 0.22 μm filtration.

The emulsion, the composition or the drug can be packaged by aseptic filling in a sterile environment, in single dose bottles, in multidose bottles that protect the solution from contamination during use, notably such as described in the following documents: WO 2008/015505, US 2009/0294347, US 2007/0210121, EP 2085068, FR 2816600, U.S. Pat. No. 5,232,687 or FR 2873358, or in any other bottle used in the topical application of drugs that avoids the use of preservatives.

According to one of its aspects, the invention relates to a unit comprising a container such as described above and an emulsion of the invention.

According to a particular embodiment, the preservative-free emulsion present in the unit is sterile and can remain sterile, for example for at least three months, notably at least six months, in particular at least one year, indeed at least three year, before opening.

Once the bottle is opened, and depending on the type of bottle, the emulsion can be used for one month, indeed for three months.

According to another of its aspects, the invention relates to a pharmaceutical composition or a drug comprising, or consisting of, an emulsion such as defined above, in particular for use in treating or preventing ocular dryness, allergies and/or inflammation of the eye, in particular related to dry eye.

According to another of its aspects, the invention relates to the use of a composition of the invention for preparing a pharmaceutical composition or a drug, in particular for use in treating or preventing ocular dryness, allergies and/or inflammation of the eye, in particular related to dry eye.

According to another of its aspects, the invention relates to an emulsion or a composition such as defined above further comprising an active compound, in particular intended to act on the eye.

According to another of its aspects, the invention relates to the use of a composition or an emulsion of the invention as a carrier for an active compound, in particular intended to act on the eye.

When this emulsion is used as a vector, it can make it possible to decrease the concentration of the active ingredient or the dosage, the number of applications and/or the period of time between two applications.

Without wanting to be bound by this theory, this can come from the fact that said emulsion, perhaps because of its viscosity and its mucoadhesive properties, improves residence time and thus increases the proportion of the active ingredient that can be delivered to the target.

According to another of its aspects, the invention also relates to the use of an emulsion or a composition of the invention as an agent to restore and/or replace the lacrimal film.

The invention relates in particular to an emulsion such as defined above and in the examples, to be used in therapeutics, in particular in treating or preventing ophthalmic diseases, more particularly in treating or preventing ocular dryness, allergies and/or inflammation of the eye.

The invention relates to a method for treating or preventing ocular dryness, allergies and/or inflammation of the eye in a subject requiring one such treatment, which consists in applying to one eye or to both eyes of said subject a suitable quantity of the inventive emulsion such as defined above and in the examples.

This emulsion is advantageously applied in the form of drops which are allowed to fall onto the eye, according to the standard methods for applying ophthalmic compositions, more particularly eye lotions. The number of drops applied during each application is generally not limiting insofar as excess emulsion is eliminated by the natural batting motion of the eyelids over the eye. The number of daily applications will depend on each subject's specific needs.

However, insofar as the composition comprises an active ingredient such as defined above, the number of drops applied and the number of daily applications will depend on the active ingredient delivered with the inventive emulsion.

According to another of its aspects, the invention relates to the use of a stabilizing polymer, optionally in combination with a phospholipid, as a stabilization agent for an emulsion comprising a lipid in the hydrophobic phase, a polysaccharide with mucomimetic or mucoadhesive properties in the hydrophilic phase, combined in an aqueous phase with the help of at least one phospholipid and at least one ionic polymer.

According to another of its aspects, the invention relates to the use of a stabilizing polymer, optionally in combination with a phospholipid, as a stabilization agent for an emulsion comprising:
 a lipid other than the phospholipid in the hydrophobic phase,
 a mucomimetic polymer in the aqueous phase, in particular at a high concentration, notably such as defined above.

According to another of its aspects, the invention relates to a method for preparing a composition or an emulsion, notably such as defined above, comprising at least the following steps:
 a) mix a phospholipid and a lipid other than the phospholipid, notably at a temperature greater than 30° C.,
 b) dissolve a mucomimetic polymer in a buffer, notably citrate,
 c) dissolve a stabilizing polymer in the aqueous phase of step b),
 d) disperse the oily phase of step a) in the aqueous phase of step c) by agitation,
 e) control and adjust the pH, notably by adding a base or an acid, in particular the base or acid form of the compound forming the buffer, and/or control and adjust the osmolarity, and
 f) sterilize the emulsion, in particular by filtering the emulsion obtained, notably using a 0.22 μm filter, in particular by maintaining it at a temperature greater than 30° C.

In particular, the agitation of step d) is strong agitation in order to obtain small drops, in particular such as defined in the present description. This agitation can be carried out with a homogenizer.

Said method can further comprise a packaging step, in particular in sterile packaging, and even more particularly in packaging that preserves the sterile emulsion, and notably the packaging is such as described above.

In particular, step a) is carried out by mixing the lipid other than the phospholipid, the phospholipid and distilled water, notably by heating to a temperature greater than 30° C., with agitation, until a homogeneous phase is obtained.

The ratio of the phospholipid to the lipid other than the phospholipid can range from 1:5 to 1:1.

The total lipid content in distilled water can be roughly 0.5% by weight in relation to the total weight of the composition.

The emulsion obtained in step a) can be sterilized by filtration, in particular using a 0.22 μm filter. The temperature can be greater than 30° C.

Step b) can be carried out by dissolving the mucomimetic polymer in a buffer, notably citrate, and by heating, notably at a temperature greater than 30° C.

During step c) it is possible to control and adjust the pH and/or the osmolarity by respectively adding citrate or citric acid and/or sodium chloride.

When it is stated that "the temperature can be greater than 30° C." it can more particularly range from 32 to 45° C., notably from 35 to 43° C., indeed from 37 to 42° C.

Particularly, this emulsion is sterilized by filtration, in particular on a 0.22 μm microbiological filter made of PP (polypropylene), PES (polyethersulfone), PTFE (polytetrafluoroethylene), PET (polyester) or PC (polycarbonate) or on any other filter suitable for sterilizing filtration.

According to one variant of the method, it is possible to further add during steps a) to e) a surfactant, or surface-active.

According to one variant of the method, it is possible during steps c) to e) to add an active ingredient for ophthalmic use, a preservative and/or an agent entering into the composition of the aqueous phase of the lacrimal film.

Of course, the various characteristics set forth in the present description can be combined.

The following examples are given to illustrate the invention.

EXAMPLES

The examples below are eye lotions containing an oil-in-water emulsion and a mucomimetic polymer, intended in particular for restoring the various layers of the lacrimal film in patients suffering from dry eye syndrome. They are prepared with the following ingredients given for a centesimal composition. These formulas have a pH of roughly 7.1 and are hypotonic to tears.

Example 1

| Oily phase: | |
|---|---|
| Triglycerides | 0.05% |
| Lecithin | 0.1% |
| Aqueous phase: | |
| Chondroitin sulfate | 0.2% |
| Polyvinyl alcohol | 0.2% |
| Citric acid | 0.05M |
| Sodium citrate | 0.05M |
| Sodium chloride | q.s. |
| Distilled water | q.s. |

Example 2

| Oily phase: | |
|---|---|
| Triglycerides | 0.2% |
| Lecithin | 0.1% |
| Aqueous phase: | |
| Sodium hyaluronate | 0.2% |
| Polysorbate | 0.2% |
| Citric acid | 0.05M |
| Sodium citrate | 0.05M |
| Sodium chloride | q.s. |
| Distilled water | q.s. |

Example 3

| Oily phase: | |
|---|---|
| Triglycerides | 0.05% |
| Lecithin | 0.1% |
| Aqueous phase: | |
| Dextran sulfate | 0.2% |
| Sodium hydroxypropylmethylcellulose | 0.2% |
| Citric acid | 0.05M |
| Sodium citrate | 0.05M |
| Sodium chloride | q.s. |
| Distilled water | q.s. |

Example 4

| Oily phase: | |
|---|---|
| Triglycerides | 0.05% |
| Lecithin | 0.1% |
| Aqueous phase: | |
| Heparin | 0.2% |
| Polyvinylpyrrolidone | 0.1% |
| Sodium carboxymethylcellulose | 0.1% |
| Citric acid | 0.05M |
| Sodium citrate | 0.05M |
| Sodium chloride | q.s. |
| Distilled water | q.s. |

Example 5

| Oily phase: | |
|---|---|
| Triglycerides | 0.05% |
| Lecithin | 0.1% |
| Aqueous phase: | |
| Sodium alginate | 0.1% |
| Polyvinyl alcohol | 0.1% |
| Sodium carboxymethylcellulose | 0.2% |
| Citric acid | 0.05M |
| Sodium citrate | 0.05M |
| Sodium chloride | q.s. |
| Distilled water | q.s. |

Example 6

| Oily phase: | |
|---|---|
| Triglycerides | 0.1% |
| Lecithin | 0.1% |
| Aqueous phase: | |
| Sodium hyaluronate | 0.2% |
| Sodium carboxymethylcellulose | 0.1% |
| Citric acid | 0.05M |
| Sodium citrate | 0.05M |
| Sodium chloride | q.s. |
| Distilled water | q.s. |

Example 7

| Oily phase: | |
|---|---|
| Triglycerides | 0.1% |
| Lecithin | 0.1% |
| Aqueous phase: | |
| Sodium hyaluronate | 0.2% |
| Sodium carboxymethylcellulose | 0.05% |

Example 8 -continued

| Aqueous phase: | |
|---|---|
| Polyvinyl alcohol | 0.1% |
| Citric acid | 0.05M |
| Sodium citrate | 0.05M |
| Sodium chloride | q.s. |
| Distilled water | q.s. |

Example 8

| Oily phase: | |
|---|---|
| Triglycerides | 0.05% |
| Lecithin | 0.1% |
| Aqueous phase: | |
| Sodium hyaluronate | 0.2% |
| Polyvinyl alcohol | 0.2% |
| Citric acid | 0.05M |
| Sodium citrate | 0.05M |
| Sodium chloride | q.s. |
| Distilled water | q.s. |

Example 9

| Oily phase: | |
|---|---|
| Triglycerides | 0.2% |
| Lecithin | 0.1% |
| Aqueous phase: | |
| Sodium hyaluronate | 0.2% |
| Polysorbate | 0.1% |
| Citric acid | 0.05M |
| Sodium citrate | 0.05M |
| Sodium chloride | q.s. |
| Distilled water | q.s. |

Example 10

| Oily phase: | |
|---|---|
| Triglycerides | 0.05% |
| Lecithin | 0.1% |
| Aqueous phase: | |
| Sodium hyaluronate | 0.2% |
| Sodium hydroxypropylmethylcellulose | 0.2% |
| Citric acid | 0.05M |
| Sodium citrate | 0.05M |
| Sodium chloride | q.s. |
| Distilled water | q.s. |

Example 11

| Oily phase: | |
|---|---|
| Triglycerides | 0.1% |
| Lecithin | 0.1% |

-continued

| Aqueous phase: | |
|---|---|
| Sodium hyaluronate | 0.2% |
| Sodium carboxymethylcellulose | 0.1% |
| Sodium hydroxypropylmethylcellulose | 0.1% |
| Citric acid | 0.05M |
| Sodium citrate | 0.05M |
| Sodium chloride | q.s. |
| Distilled water | q.s. |

Example 12

| Oily phase: | |
|---|---|
| Triglycerides | 0.05% |
| Lecithin | 0.1% |
| Aqueous phase: | |
| Sodium hyaluronate | 0.2% |
| Sodium carboxymethylcellulose | 0.1% |
| Polyvinylpyrrolidone | 0.1% |
| Citric acid | 0.05M |
| Sodium citrate | 0.05M |
| Sodium chloride | q.s. |
| Distilled water | q.s. |

Example 13

| Oily phase: | |
|---|---|
| Triglycerides | 0.05% |
| Lecithin | 0.1% |
| Aqueous phase: | |
| Sodium hyaluronate | 0.2% |
| Sodium carboxymethylcellulose | 0.1% |
| Polyvinyl alcohol | 0.1% |
| Citric acid | 0.05M |
| Sodium citrate | 0.05M |
| Sodium chloride | q.s. |
| Distilled water | q.s. |

The invention claimed is:

1. An eye lotion being a stable oil-in-water emulsion, without surfactants other than phospholipid, having an osmolarity of 110 to 180 mOsm/l said oil-in-water emulsion comprising:
   at least one mucomimetic polymer selected from glycosaminoglycans and hyaluronic acids,
   at least one phospholipid,
   at least one lipid other than the phospholipid, which is a triglyceride whose three hydroxyl groups are esterified by fatty acids comprising from 8 to 12 carbon atoms,
   at least one stabilizing polymer selected from cellulose polymers,
   water, and
   a salt selected from potassium chloride, sodium chloride or potassium and/or sodium carbonate.

2. The eye lotion according to claim 1 wherein said eye lotion has a viscosity lower than or equal to $10^{-1}$ Pa·s.

3. The eye lotion according to claim 1 wherein said eye lotion has a turbidity of 0 to 5,000 NTU.

4. The eye lotion according to claim 1 wherein said eye lotion comprises from 0 to 10 ppm of preservatives and/or EDTA.

5. The eye lotion according to claim 1 wherein said phospholipid is present in a concentration of 0.01% to 3% by weight in relation to the total weight of the composition and wherein said phospholipid is selected from phosphoacylglycerides, phosphosphingolipids, phosphonosphingolipids, phosphoglycolipids and phosphosaccharolipids.

6. The eye lotion according to claim 1 wherein said phospholipid is selected from lecithins.

7. The eye lotion according to claim 1 wherein said eye lotion comprises a lipid other than the phospholipid in a concentration of 0.01% to 5% by weight in relation to the total weight of the composition and wherein said lipid other than the phospholipid is a glyceride.

8. The eye lotion according to claim 1 wherein said eye lotion comprises a stabilizing polymer in a concentration of 0.01% to 5% by weight in relation to the total weight of the composition.

9. The eye lotion according to claim 1 wherein said cellulose polymer is carboxymethylcellulose.

10. The eye lotion according to claim 1 wherein said mucomimetic polymer is present in a concentration of 0.01% to 5% by weight in relation to the total weight of the composition.

11. The eye lotion according to claim 1 wherein said eye lotion has a pH of 5.5 to 8.

12. The eye lotion according to claim 1 further comprising an active agent selected from the group consisting of antiseptics, antibiotics, antivirals, anti-inflammatories, anti-allergy agents, anti-glaucoma agents, anti-dryness agents, vasoconstrictors, anesthetics, mydriatics, miotics, diagnostic products, products for treating retinal diseases and combinations thereof.

13. The eye lotion according to claim 1 further comprising a substance helping to restore the composition of the lacrimal film's aqueous layer selected from the group consisting of vitamin A, vitamin B, vitamin B12, albumin, sodium, potassium, calcium, chloride, bicarbonate ions, buffer composition and combinations thereof.

14. An eye lotion being a stable oil-in-water emulsion, without surfactants other than phospholipid, having an osmolarity of 110 to 180 mOsm/l, and comprising:
   0.01 to 5% by weight of at least one mucomimetic polymer, said mucomimetic polymer being selected from glycosaminoglycans and hyaluronic acids,
   0.01 to 3% by weight of at least one phospholipid, said phospholipid being selected from phosphoacylglycerides, phosphosphingolipids, phosphonosphingolipids, phosphoglycolipids and phosphosaccharolipids,
   0.01 to 5% by weight of at least one lipid other than the phospholipid, said lipid other than the phospholipid which is a triglyceride whose three hydroxyl groups are esterified by fatty acids comprising from 8 to 12 carbon atoms,
   0.01% to 5% by weight of at least one stabilizing polymer, said stabilizing polymer being selected from cellulose polymers,
   from 0 to 10 ppm of preservatives and/or EDTA, and
   a salt selected from potassium chloride, sodium chloride or potassium and/or sodium carbonate
   water.

15. The eye lotion according to claim 14 wherein said eye lotion has a viscosity lower than or equal to $10^{-1}$ Pa·s.

16. The eye lotion according to claim 14 further comprising an active agent selected from the group consisting of antiseptics, antibiotics, antivirals, anti-inflammatories, anti-allergy agents, anti-glaucoma agents, anti-dryness agents, vasoconstrictors, anesthetics, mydriatics, miotics, diagnostic products, products for treating retinal diseases and combinations thereof.

17. The eye lotion of claim 1 further including at least one buffer selected from the group consisting of phosphate buffer, acetate buffer and citrate buffer.

18. The eye lotion of claim 14 further including at least one buffer selected from the group consisting of phosphate buffer, acetate buffer and citrate buffer.

19. The eye lotion of claim 1 having a weight ratio of lipid other than phospholipid to phospholipid between 0.2 to 5.0.

20. The eye lotion of claim 14 having a weight ratio of lipid other than phospholipid to phospholipid between 0.2 to 5.0.

21. A method for treating ophthalmic diseases comprising administering in the eye(s) of a patient in need thereof an efficient amount of the eye lotion according to claim 1.

22. A method for treating ocular dryness, allergies and/or inflammation of the eye comprising administering in the eye(s) of a patient in need thereof an efficient amount of the eye lotion according to claim 1.

23. A method for preparing an eye lotion according to claim 1, said method comprising the following steps:
   a) mix the at least one phospholipid and the at least one lipid other than the phospholipid which is a triglyceride whose three hydroxyl groups are esterified by fatty acids comprising from 8 to 12 carbon atoms,
   b) dissolve the at least one mucomimetic polymer in a buffer,
   c) dissolve the at least one stabilizing polymer in the aqueous phase of step b),
   d) disperse the oily phase of step a) in the aqueous phase of step c) by agitation,
   e) control and adjust the pH by adding respectively a base or an acid and/or control and adjust the osmolarity, and
   f) sterilize the emulsion.

24. The method of claim 23, wherein the eye lotion is sterilized by filtration.

25. The method of claim 24, wherein the eye lotion is filtered on a 0.22 μm filter.

* * * * *